United States Patent [19]
Adair

[11] 3,995,642
[45] Dec. 7, 1976

[54] METHOD AND APPARATUS FOR RETAINING A DRAIN TUBE WITHIN A URETER

[75] Inventor: Edwin L. Adair, Littleton, Colo.

[73] Assignee: Medical Dynamics, Inc., Littleton, Colo.

[22] Filed: Apr. 3, 1975

[21] Appl. No.: 564,792

[52] U.S. Cl. .......................................... 128/349 R
[51] Int. Cl.² ....................................... A61M 25/00
[58] Field of Search .......... 128/348, 349 R, 350 R, 128/DIG. 26

[56] References Cited
UNITED STATES PATENTS

| | | | |
|---|---|---|---|
| 1,880,964 | 10/1932 | Kunsztler | 128/356 |
| 2,212,334 | 8/1940 | Wallerich | 128/349 R X |
| 2,707,958 | 5/1955 | Davis | 128/349 R |
| 3,730,187 | 5/1973 | Reynolds | 128/349 R |
| 3,783,454 | 1/1974 | Sausse et al. | 128/350 R X |
| 3,938,529 | 2/1976 | Gibbons | 128/349 R |

*Primary Examiner*—Dalton L. Truluck

[57] ABSTRACT

Tube adapted to be disposed within a ureter for drainage from a kidney to the bladder, characterized by a cord or suture member secured to its lower end and lying along same to a point of securement, preventing movement of the tube into the bladder.

3 Claims, 4 Drawing Figures

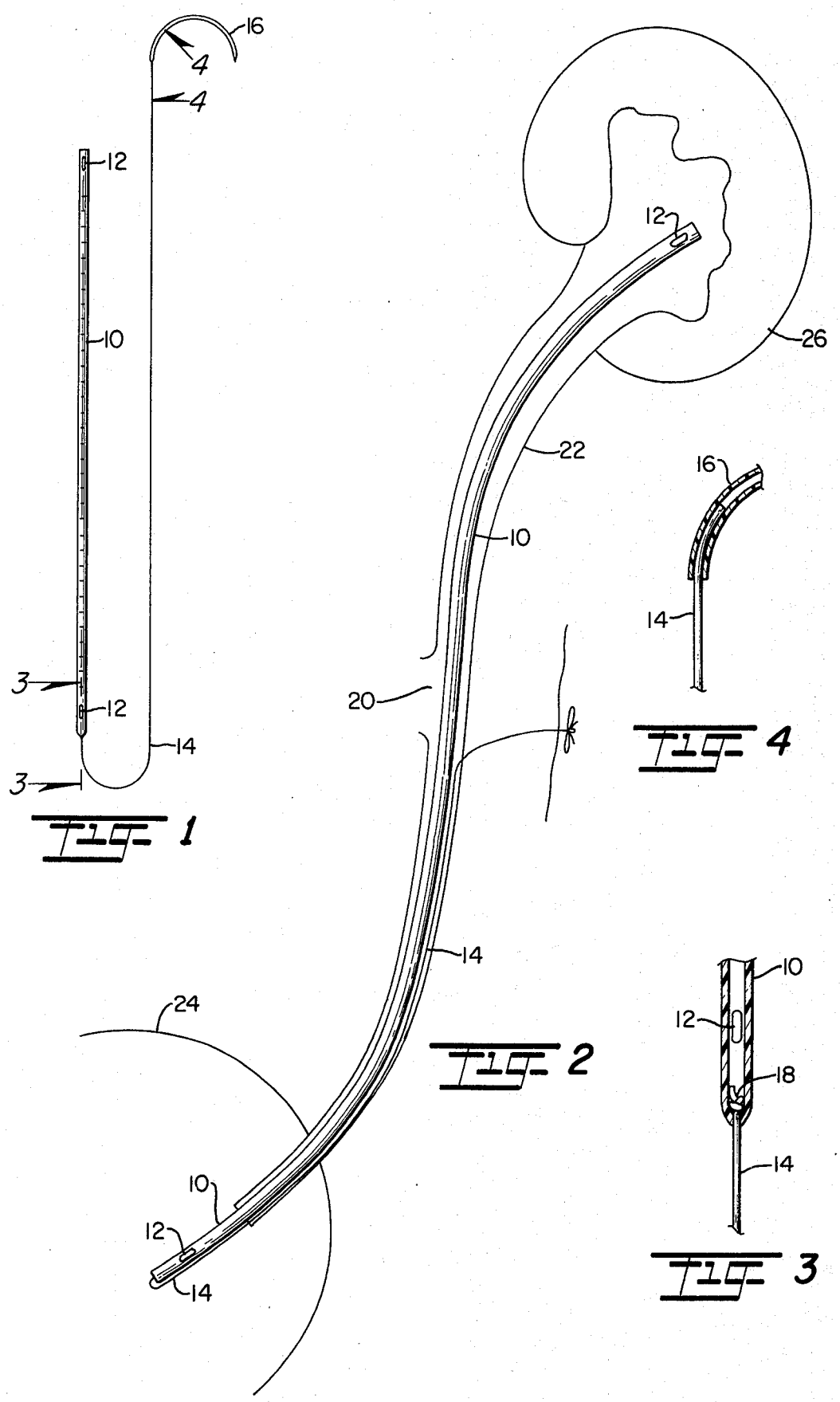

METHOD AND APPARATUS FOR RETAINING A DRAIN TUBE WITHIN A URETER

BACKGROUND OF THE INVENTION

In surgical operations of the ureter it is conventional practice to make an incision in the wall of the ureter to provide access for the removal of an obstruction, such as a tumor, scar or kidney stone. A temporary tube may then be inserted in the ureter, the ends of which communicate with a kidney and bladder. Upon healing of the ureter incision, the tube is removed by capturing its lower bladder end by a cystoscope instrument. It is also conventional to improvise the requisite tube during the operation.

One of the disadvantages of the procedure, aforesaid, is that the tube tends to move by peristalsis into the bladder, where it may be difficult to capture with a cystoscope. A further disadvantage is that such movement may occur before the ureter, or incision therein, has completely healed, thus subjecting it to undesired flow of fluid through or adjacent unhealed portions thereof.

To obviate such disadvantages it becomes apparent that the disiderata would be to prevent movement of the tube from its intended position in the ureter until the optimum time for its removal and also to retain its lower or proximate end in such position in the bladder where it may more readily be captured for removal.

SUMMARY OF THE INVENTION

The subject of the invention provides the disiderata just referred to, and is characterized by a tube adapted to extend through a ureter from a kidney to the bladder and having a cord or suture secured thereto adapted to be fixed to the body to retain it in the ureter and prevent movement thereof toward the bladder until it is detached from its point of affixation, after which it and the tube may be withdrawn from the ureter. The tube is sufficiently flexible to enable one end portion to be moved through an incision in the wall of the ureter and into the bladder and its other end portion to be similarly moved through the incision and into a kidney. Preferably, the tube is impregnated with a substance, such as barium sulphate, which is opague to X-rays so that its orientation within the ureter, the kidney, and bladder may be determined. To obviate improvisation during an operation, as previously referred to, the tube may be prefabricated in various lengths and diameters so that an optimum size may be selected to meet the requirements of the particular patient. An additional feature resides in the optional use of graduations on the tube which indicate distances of insertion thereof from the incision so that the position of the ends of the tube in the kidney and bladder may be closely estimated.

The general objects of the invention include, accordingly, the features briefly set forth above.

Further objects, advantages, and salient features will become more apparent from the detailed description to follow, the accompanying claims, and the appended drawing, to now be briefly described.

BRIEF DESCRIPTION OF THE DRAWING

FIG. 1 is a side elevation of the subject of the invention;

FIG. 2 diagrammatically illustrates the invention when disposed in a ureter with its ends communicating a kidney and bladder;

FIG. 3 is an enlarged section taken on line 3—3, FIG. 1; and

FIG. 4 is an enlarged section taken on line 4—4, FIG. 1.

DETAILED DESCRIPTION OF PREFERRED EMBODIMENT

Referring now to the drawing, the subject of the invention comprises a flexible plastic tube 10 having apertures 12,12 or a series of apertures adjacent its ends and a cord or suture 14 of nylon or other suitable material, secured to its lower end. The other end of the suture may or may not have a needle 16 secured thereto.

As best shown in FIG. 3, the lower or proximate end of tube 10 is necked down and suture 14 is provided with a knot 18 to prevent the suture from pulling out of the tube. The suture may be heat sealed to the tube, or solvent welded or adhesive bonded thereto. This necked down end also provides a slightly tapered end which facilitates movement into the ureter as distinguished from a sharp end of the same diameter of the tube.

As best shown in FIG. 4, needle 16 is hollow, except at its point, and suture 14 is secured within the hollow needle, this construction being preferable to eliminate an eye in the needle and a fold of the suture therethrough which would provide an enlargement which would be somewhat more difficult to draw through tissue of a patient. Securement of the suture may be effected with cement or crimping the hollow needle onto the suture.

In the use of the invention, and with reference to FIG. 2, an incision 20 is made at a desired point in ureter 22 to provide access for removal of an obstruction, such as a tumor or calculus. The lower end of tube 10, with the suture lying along same, is then inserted through the incision and moved through ureter 22 to the position shown with its lower end within bladder 24. The upper portion of tube 10 is then inserted through the incision and moved to the position shown with its upper end within kidney 26. Needle 16 is then passed through the wall of the ureter, and then through tissue or flesh to a point outside of the body where the suture is suitably tied to prevent movement of the tube into the bladder. Incision 20 is then closed with a suture in a manner conventional in the art. As will be apparent during healing of the ureter, fluid may pass from the kidney to the bladder through tube 10. After healing, suture 14 is severed or released at its point of securement, the lower end of tube 10 is located and grasped with a cystoscope instrument and tube 10 and its attached suture 14 are removed, permitting the ureter to perform its normal drainage function.

An optional feature includes graduations or other indicia on the tube as shown in FIG. 1 for determining the distance of the tube ends from the incision. Another optional feature is the provision of a substance, such as barium sulfate, impregnated in the tube material, which is opaque to x-rays, whereby the tube position may be precisely determined at the time of the operation or may be monitered thereafter. A further optional feature (not shown) is the provision of various tips, such as bullet, filiform and olive tips which may be secured within the distal end of the tube.

What is claimed is:

1. A method of preventing a drainage tube, disposed in a ureter and extending between a kidney and the bladder wherein its proximate end within the bladder is readily accessible by a cystoscope for removing the tube from the ureter, from moving by perstalsis toward the bladder to a position in which the proximate end thereof is difficulty accessible by a cystoscope for capturing same, the tube adapted to be installed in the position aforesaid through an incision in the ureter, said method comprising;
 a. attaching one end of a flexible cord to the tube at a position between the incision and its proximate end,
 b. inserting the tube through the incision and through the ureter into the bladder, the tube pulling the cord therewith,
 c. threading the cord through the wall of the ureter in the locus of the incision and through body tissue to a position exteriorly of the body, and
 d. affixing the cord exteriorly of the body for preventing movement of the tube toward the bladder.

2. A method in accordance with claim 1 including the step of releasing affixation of the cord to the body when it is desired to remove the tube from the ureter, whereby the cord may reversely move through the body tissue and into the ureter for removal of the tube and cord through the bladder.

3. A body drainage device comprising, in combination, a drainage tube having a proximate end and a distal end and adapted to be inserted through an incision in the wall of a ureter between ends thereof and to be disposed with the distal end thereof in a kidney and the proximate end thereof at a position in the bladder where it is readily accessible by a cystoscope for removing the tube from the ureter, the tube being subject to movement by peristalsis toward the bladder to a position in which the distal end thereof is difficulty accessible by a cystoscope for capturing same, the proximate end of the tube to be positioned in the bladder being inwardly tapered to facilitate the insertion of the tube through the ureter and toward the bladder, a flexible cord or surgical suture fixedly attached inwardly of the tube between its approximate center and its proximate end and adapted to extend upwardly within the ureter and adjacent the tube, a portion of said cord adapted to extend through the wall of the ureter and body tissue at a point opposite a point between the ends of the tube when inserted, and to be releasably affixed to the body exteriorly thereof for preventing movement of the tube downwardly toward the bladder, said cord, when released from its fixation to the body, permitting the tube and cord to be withdrawn from the ureter downwardly through the bladder and urethra, at least one aperture in the wall of the tube near its proximate end through which fluid may flow to the bladder, at least one aperture in the wall of the tube near its distal end for entry of fluid from the kidney, the distal end of the tube to be placed in the kidney being inwardly tapered to facilitate insertion of a tube through the ureter and toward the kidney, a needle fixedly attached at one end to the free end of the cord for pulling the end of the cord to a locus exterior of the body, said tube being fabricated in various lengths and diameters to thereby permit selection of an optimum size to meet requirements of various patients.

* * * * *